United States Patent [19]

Morgan

[11] Patent Number: 4,938,775
[45] Date of Patent: Jul. 3, 1990

[54] ARTIFICIAL LEG WITH BEARINGS FOR ROTATIONAL MOTION

[76] Inventor: Robert D. Morgan, 5711 West Ave. M, #33, Quartz Hill, Calif. 93536

[21] Appl. No.: 331,957

[22] Filed: Apr. 3, 1989

[51] Int. Cl.$^5$ ................. A61F 2/60; A61F 2/62/2/66
[52] U.S. Cl. ..................................... 623/27; 623/38; 623/49
[58] Field of Search ..................................... 623/27–55

[56]  References Cited

U.S. PATENT DOCUMENTS

| | | | |
|---|---|---|---|
| 433,497 | 8/1890 | Swank | 623/48 |
| 1,937,870 | 12/1933 | Carnes | 623/49 |
| 3,707,731 | 1/1973 | Morgan | 623/55 |
| 4,499,613 | 2/1985 | Yarrow | 623/48 |
| 4,564,365 | 1/1986 | Winer | 623/38 |

FOREIGN PATENT DOCUMENTS 2110936  6/1983  United Kingdom ................. 623/49

Primary Examiner—Randall Green
Assistant Examiner—David H. Willse
Attorney, Agent, or Firm—Robert M. Sperry

[57] ABSTRACT

An improved artificial leg comprising a socket fitted to mate comfortably to an amputee's stump and having a vise-like attaching member mounted thereon, a stem portion having an attaching portion adapted for releasable mating with the attaching member of the socket and having a foot member comprising a semi-spherical ring secured to the lower end of the stem, a generally semi-spherical base member rotatably secured to the ring, a resilient sole covering the bottom of the base member and a boot formed of resilient material secured to the stem and serving to normally urge the base member to a predetermined position with respect to the stem.

18 Claims, 5 Drawing Sheets

ARTIFICIAL LEG WITH BEARINGS FOR ROTATIONAL MOTION

BACKGROUND

1. Field of Invention

This invention relates to artificial feet and is particularly directed to an artificial foot having quick release means for attaching said foot to a socket and having self-centering foot means for keeping said foot properly aligned with the leg portion thereof.

2. Prior Art

Artificial legs and other artificial devices of this category in the prior art have a fairly typical construction. Thus, a typical artificial leg comprises a socket which is fitted to the amputee's stump and a joint is provided at the knee which provides a hinge comparable to that of a natural knee. The hinge may be of a ball and socket type. Typically, there is an artificial foot at the end of the leg attached to it by a joint. This joint may also be a ball and socket joint. When fitted with such an artificial leg, the amputee is enabled to walk and perform various activities, but within quite stringent limitations. Obviously, the amputee does not have the control of the knee joint that he would have with a natural leg. Furthermore, the artificial foot must, of course, be aligned with the leg and, of course, there is no control for this comparable with that of a natural foot. This imposes very severe limitations when activities requiring any significant degree of freedom of motion are considered.

To overcome these limitations, it has been proposed to provide an artificial leg in the form of a stem or peg, having no knee joint, and having a generally semi-spherical member secured to the distal end of the stem in lieu of a foot. Such a device is covered by my prior patent, U.S. Pat. No. 3,707,731, issued Jan. 2, 1973. With this structure, the semi-spherical member is symmetrical about the stem or leg so that there is no problem of alignment and the stem is attached to the socket through a bearing which provides for 360° of rotation. Hence, the position of the semi-spherical "foot" is always relatively the same. Moreover, the semi-spherical "foot" is constructed to provide a shock absorbing effect and to allow angular tilting of the "foot" relative to the stem or leg. It has been found that this structure provides vastly greater and more reliable support in playing golf or in similar athletic activities.

Although the device of my prior patent provides considerable functional improvement over conventional artificial legs. It has been found that it does not adjust to tilted surfaces as rapidly as might be desired and does not always return to its original position as rapidly as might be desired when it is lifted from the tilted surface. Furthermore, although the artificial leg of my prior patent has numerous functional advantages for the amputee, it is not as aesthetically attractive as a conventional artificial foot. Thus, for social purposes, the conventional artificial foot may be desirable. It would be highly desirable for the amputee to be able to rapidly switch, as desired, from the more functional "peg" of my prior patent to the more aesthetic conventional foot. Unfortunately, as noted above, artificial legs conventionally include a socket which is fitted to the amputee's stump. Thus, when not attached for use, an artificial leg is a bulky and cumbersome device and it would be quite burdensome and annoying to be required to carry one while wearing another.

A search in the United States Patent Office has revealed the following references:

| U.S. PAT. NO. | INVENTOR | ISSUED |
| --- | --- | --- |
| 3,706,465 | E. J. Olowinski | Dec. 19, 1972 |
| 3,906,552 | A. L. Weber | Sep. 23, 1975 |
| 4,007,496 | R. Glabiszwski | Feb. 15, 1977 |
| 4,564,365 | R. A. Winer et al | Jan. 14, 1986 |

The patent to Winer et al teaches a quick change mechanism for permitting the rapid exchange of artificial legs. However, the Winer et al mechanism is complex and is not designed to provide strong omnidirectional support as is needed for athletic activities. Furthermore, substantial modification and precise refitting of an existing artificial leg would be required to enable its use with the quick change mechanism of Winer et al. Thus, none of the prior art artificial legs have been entirely satisfactory.

BRIEF SUMMARY AND OBJECTS OF INVENTION

These disadvantages of prior art artificial legs are overcome with the present invention and an improved artificial leg is provided having a socket embodying a quick release fitting mating with a member which can be quickly and easily mounted on an existing artificial leg and having a stem with a semi-spherical foot member which is quickly and easily attachable to said socket and which can adjust quickly and easily to a tilted surface and which returns promptly to its original position when the foot is lifted from the tilted surface.

The advantages of the present invention are preferably attained by providing an improved artificial leg comprising a socket fitted to mate comfortably to an amputee's stump and having a vise-like attaching member mounted thereon, a stem portion having an attaching portion adapted for releasable mating with the attaching member of the socket and having a foot member comprising a semi-spherical ring secured to the lower end of the stem, a generally semi-spherical base member rotatably secured to the ring, a resilient sole covering the bottom of the base member and a boot formed of resilient material secured to the stem and serving to normally urge the base member to a predetermined position with respect to the stem.

Accordingly, it is an object of the present invention to provide an improved artificial leg.

Another object of the present invention is to provide an improved artificial leg having improved means for quick replacement with another artificial leg.

A further object of the present invention is to provide an improved artificial leg having considerable functional utility for an amputee, yet being quickly and easily replaceable by an aesthetically attractive artificial leg when desired.

An additional object of the present invention is to provide an improved artificial leg comprising a stem having a generally semi-spherical foot member which can adapt rapidly to a tilting surface.

Another object of the present invention is to provide an improved artificial leg comprising a stem having a generally semi-spherical foot member which can adapt rapidly to a tilting surface and which will promptly return to a predetermined position when the foot is lifted from said tilted surface.

A specific object of the present invention is to provide an improved artificial leg comprising a socket fitted to mate comfortably to an amputee's stump and having a vise-like attaching member mounted thereon, a stem portion having an attaching portion adapted for releasable mating with the attaching member of the socket and having a foot member comprising a semispherical ring secured to the lower end of the stem, a generally semi-spherical base member rotatably secured to the ring, a resilient sole covering the bottom of the base member and a boot formed of resilient material secured to the stem and serving to normally urge the base member to a predetermined position with respect to the stem.

These and other objects and features of the present invention will be apparent from the following detailed description, taken with reference to the figures of the accompanying drawings.

DETAILED DESCRIPTION OF THE INVENTION

Figure 1:
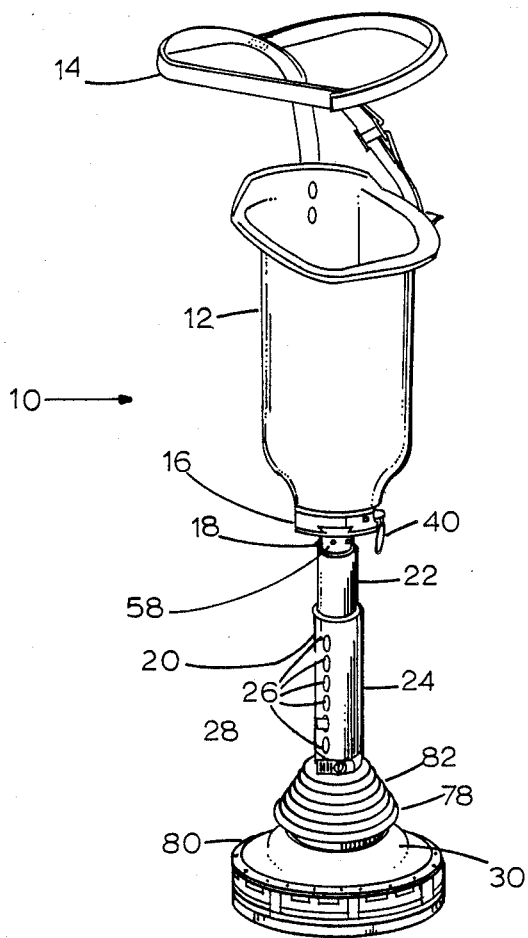
FIG. 1 is a diagrammatic representation of an artificial leg embodying the present invention.

In that form of the present invention chosen for purposes of illustration in the drawing, FIG. 1 shows an artificial leg, indicated generally at 10 comprising a socket 12 formed of suitable plastic or composite material and molded to fit the stump, not shown, of an amputee. Straps 14 serve to secure the artificial leg 10 to the wearer. A vise-like attaching member 16 is permanently attached to the lower end of the socket 12 and serves to releasably retain the attaching portion 18 of a removable support prosthesis, such as a leg or stem 20. As seen in FIG. 1, the leg or stem 20 comprises an upper tubular member 22 and a lower tubular member 24 which mates telescopically with the upper member 22 and has means, such as holes 26 and resilient buttons 28, for permitting adjustment of the length of the stem 20. A generally semi-spherical "foot" member 30 is pivotally secured to the lower end of the stem 20 and a sleeve or boot 78 is secured to the stem 20 above the foot member 30 and serves to urge the foot member 30 to a predetermined position with respect to the stem 20.

Figure 5:
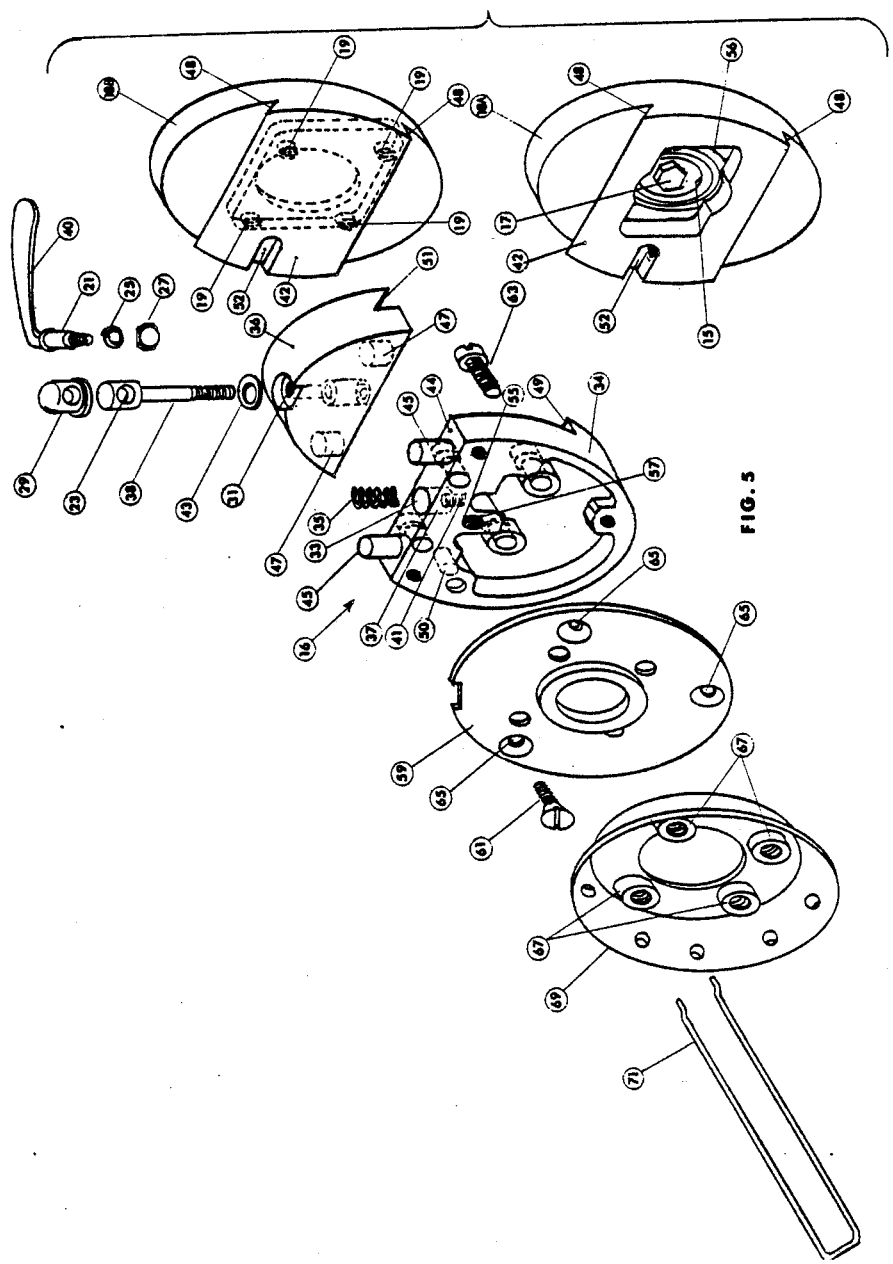
FIG. 5 is an exploded view of the attaching means of the artificial leg of FIG. 1.
Figure 6:
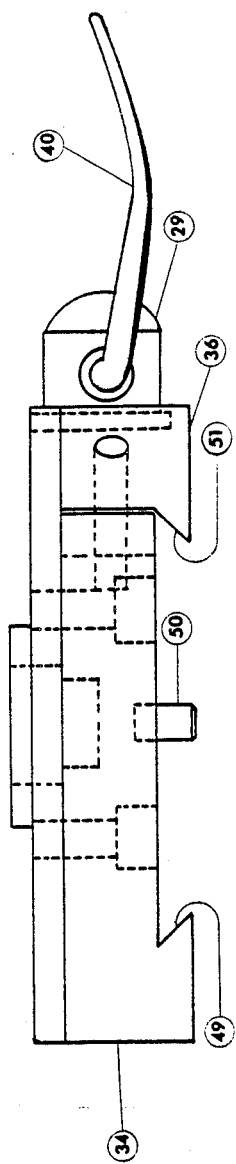
FIG. 6 is a side view of the vise-like attaching member of the artificial leg of FIG. 1.
Figure 7:
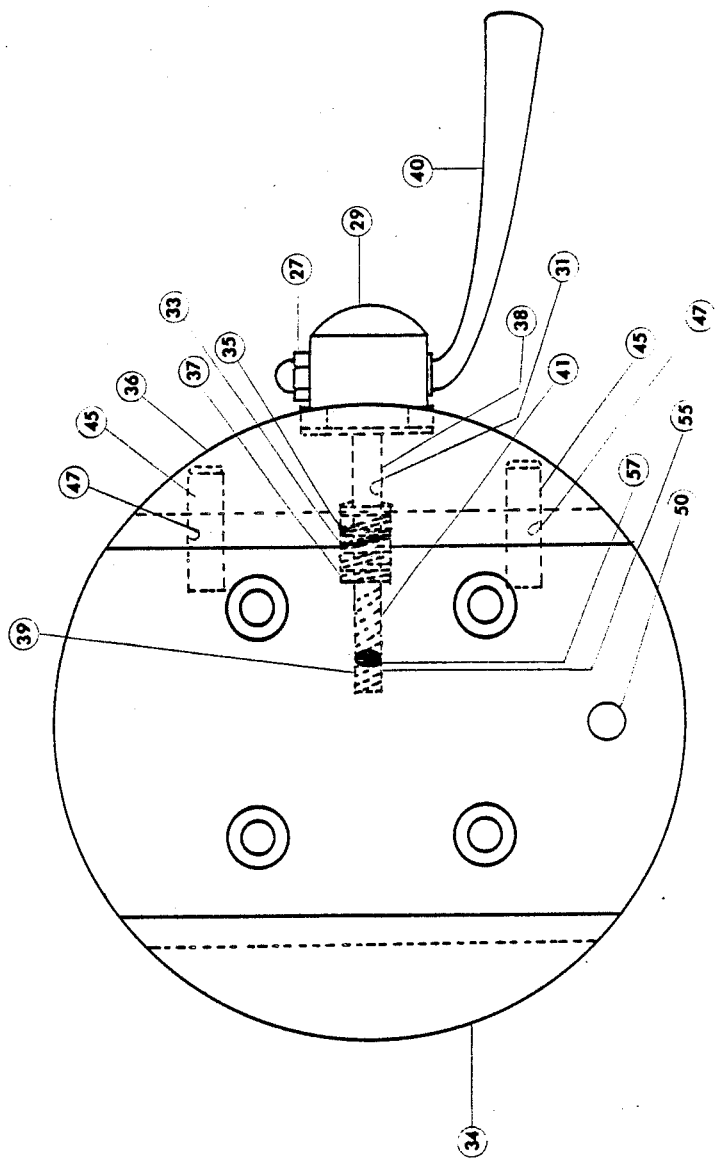
FIG. 7 is a bottom view of the vise-like attaching member of FIG. 6.
Figure 8:
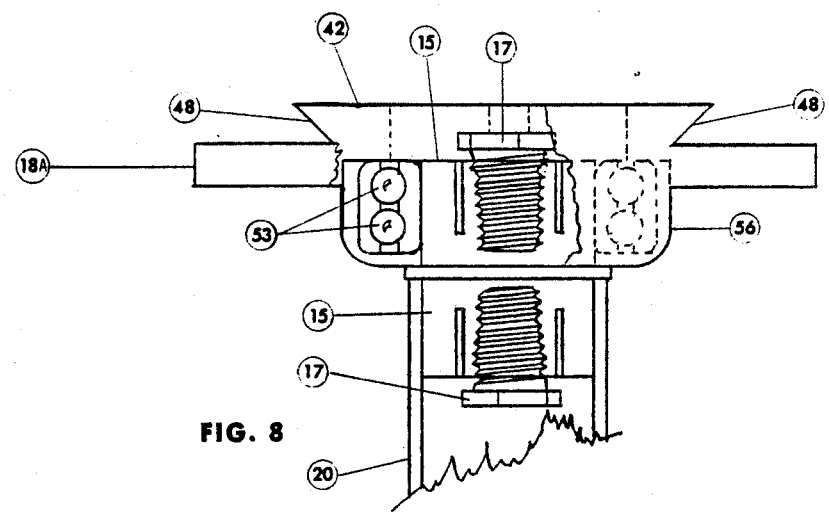
FIG. 8 is a side view, partly in section, showing the attaching portion used with the support prosthesis of FIG. 1.
Figure 9:
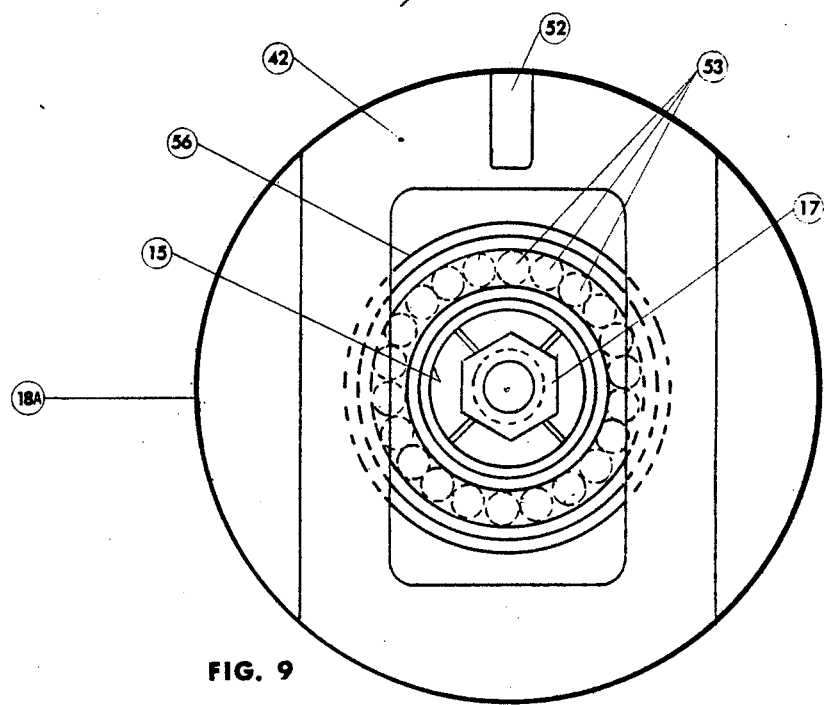
FIG. 9 is a top view of the attaching portion of FIG. 8.

As best seen in FIGS. 1, 2, 3, 5, 6, 7 and the attaching member 16 comprises a fixed portion 34 which is permanently secured to the lower end of the socket 12 and a movable portion 36 which is adjustably secured to the fixed portion 34 by suitable means, such as bolt 38, which is positionable, as by handle 40, to engage and clamp the attaching projection 42 a desired one of the attaching portions 18A or 18B, as seen in FIG. 5, so as to securely, yet releasably, attach the leg or stem 20 to the socket 12. As best seen in FIGS. 5, 6 and 7, the attaching portions 18A and 18B each carry an attaching projection 42 which is retainable by the attaching member 16 to secure a support prosthesis to the socket 12. Attaching portion 18B is provided with four bolt holes 19 for rigidly mounting the attaching portion 18B to the upper end of a cosmetic support prosthesis, such as one simulating a normal foot. In contrast, attaching portion 18A is mounted on the support prosthesis 20 of FIG. 1 and is provided with bearing member 56, as best seen in FIGS. 8 and 9, to permit free rotation of the support prosthesis 20, with respect to the socket 12, through a full 360 degrees. The handle 40 of the attaching member 16 is generally L-shaped, as best seen in FIG. 5, and has a lateral portion 21 which extends through a hole 23, formed adjacent the outer end of bolt 38, and is secured by a lock washer 25 and nut 27. If desired, an apertured cap 29 may be provided over the outer end of the bolt 38. As seen in FIGS. 5, 6 and 7, the shaft of the bolt 38 passes through a tunnel 31, formed in the movable portion 36, and projects into a stepped recess 33 formed in the facing edge 44 of the fixed portion 34. A spring 35 seats on the step 37 of the recess 33 and serves to normally urge the movable portion 36 away from the fixed portion 34. The inner end of the bolt 38 is threaded, as seen at 39 in FIGS. 5 and 7, and projects into the narrowed portion 41 of the stepped recess 33 which is also threaded. Finally, a spring washer 43 is provided about the shaft of the bolt 38 to allow for tolerance differences between the fixed portion 34 and the movable portion 36. Also, edge 44 of the fixed portion 34 is provided with a pair of projecting studs 45 which are slidably receivable by recesses 47 of the movable portion 36 to guide movement of the movable portion 36 toward and away from the fixed portion 34. The handle 40 normally lies perpendicular to the axis of the bolt 38 and rotation of the handle 40 counter-clockwise about the axis of the bolt 38 serves to move the movable portion 36 toward or away from the fixed portion 34 to permit immediate release of the attaching projection 42 and, hence, to permit removal of the leg or stem 20. Relating the handle 40 in the opposite direction serves to clamp the attaching projection 42 is a vise-like manner to instantly lock the leg or stem 20 in place. As shown, the facing edges 44 and 46 of the fixed portion 34 and movable portion 36, respectively, are formed with sections 49 and 51 which are inclined outwardly and upwardly and the sides 48 of the attaching projection 42 of the attaching portion 18 of the leg or stem 20 are correspondingly inclined so as to mate with the inclined sections 49 and 51 of the edges 44 and 46 to provide a secure, yet releasable, connection of the leg or stem 20 to the socket 12. A pin 50 projects downwardly from the fixed portion 34 and mates with a recess 52 formed in the attaching projection 42 to assure that the attaching projection is fully seated in the attaching member 16 and to assure proper orientation of the attaching projection 42 with the attaching member 16. This is important when a cosmetic leg is attached by attaching portion 18B to the attaching member 16 in order to assure proper orientation of the conventional foot. In contrast, as seen in FIGS. 5, 8 and 9, the attaching portion 18A is provided with the bearing member 56, containing two rows of ball bearings 53, and is secured to the upper end of the stem 20 by suitable means, such as expansion sleeves 15 and bolts 17. This location of the bearing member 56, as a part of the attaching portion 18A which is mounted on the support prosthesis, is extremely important because it permits free rotation of the stem 20, with respect to the socket 12, through a full 360° without transferring the rotational torque from the stem 20 to the socket 12 and, hence, to the amputee's stump. In consequence of this, friction on the amputee's stump is greatly reduced and it is found that the amputee can wear the artificial leg 10 of the present invention comfortably for extremely long periods. Furthermore, the free rotation of the stem 20, permitted by the bearing member 56, allows the foot member 30 of the present invention to adjust itself to irregularities in the ground surface without transferring the friction of such adjustments to the socket 12 and the amputee's stump. This provides greatly enhanced security of "footing" for the wearer, while significantly reducing the abrasion and fatigue which amputees usually experience from wearing prior art artificial legs.

Turning again to FIG. 5, the fixed portion 34 is provided with a vertical bore 55 which intersects the narrow portion 41 of the stepped recess 33 and a nylon insert 57 is mounted in the bore 55 to engage the inner end of the bolt 38 to prevent undesired rotation of the bolt 38 and, hence, prevent accidental loosening of the attaching member 16. A cover plate 59 is mounted on the upper surface of the fixed portion 34 and is secured by suitable means, such as bolts 61 and 63. Bolts 63 project through openings 65 in the cover plate 59 to engage suitable bosses 67 of a laminate insert plate 69 which is molded into the socket 12 to permit mounting the attaching member 16 to the socket 12. The laminate insert plate 69 is provided with a plurality of openings about the periphery thereof which receive the ends of a plurality of generally U-shaped support members 71 which are also molded into the socket 12 and serve to evenly distribute the loads transmitted by the artificial leg 10 to the socket 12.

Figure 3:
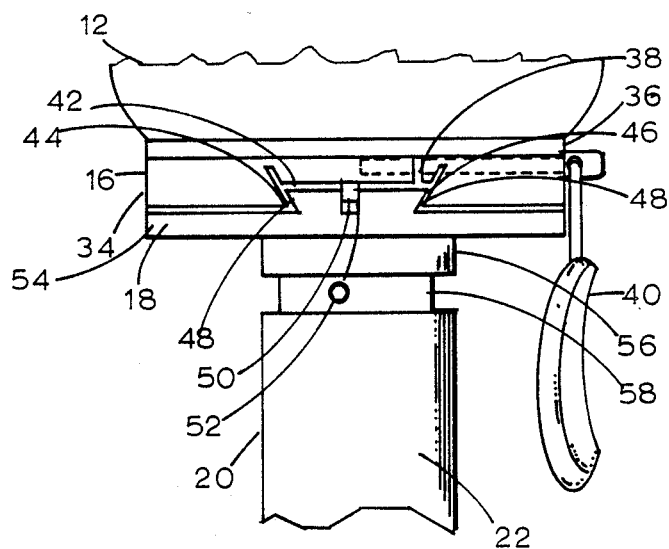
FIG. 3 is a vertical section through the attaching portion of the stem of the artificial leg of FIG. 1.

The attaching projection 42 extends upwardly from an attaching plate 54 which is fixedly mounted atop a bearing member 56, as best seen in FIG. 3, which permits free 360° rotation of a central shaft 58 to which the upper tubular member 22 of the stem 20 is fixedly attached by suitable means, not shown. In order to attach a conventional artificial leg, not shown, to the attaching member 16, an attaching plate, identical to attaching plate 54 and having an attaching projection identical to projection 42, is fixedly attached to the upper end of the conventional artificial leg above the knee joint. This permits the conventional artificial leg to be releasably attached to the socket 12 in lieu of the stem 20 when aesthetic appearance is of greater importance than the increased utility of the stem 20.

Figure 4:
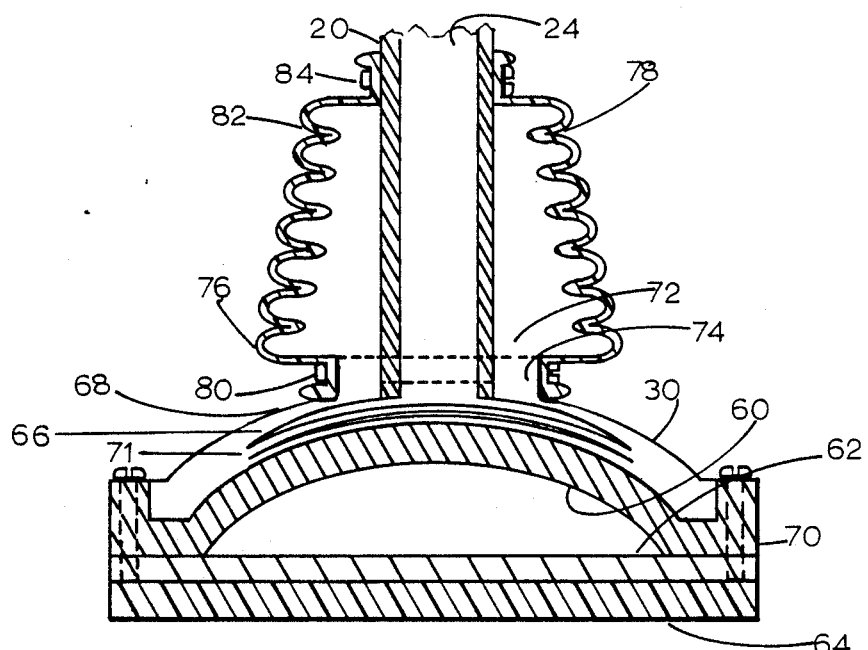
FIG. 4 is a vertical section through the foot member of the artificial leg of FIG. 1.
Figure 2:
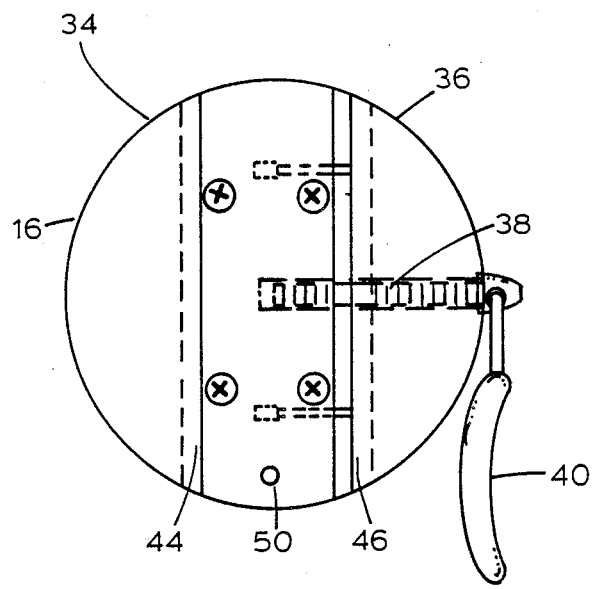
FIG. 2 is a bottom view of the attaching member of the artificial leg of FIG. 1.

As seen in FIG. 4, the increased utility of the stem 20 is obtained by providing a generally semi-spherical foot 30 comprising a generally semi-spherical base member 60 having a base plate 62 covering the bottom of the base member 60 and faced with a sole 64 formed of a suitable material, such as rubber, which will provide a cushioning or shock absorbing function and will also serve to resist slipping. If desired, the sole 64 may be provided with a tread design to enhance slip resistance. To attach the foot 30 to the lower end of the stem 20, a semi-spherical ring 66 is fixedly secured to the lower end of the lower tubular member 24 and has a peripheral chord of somewhat lesser length than that of the base member 60. A generally semi-spherical retainer member 68 is secured to a peripheral flange 70 on the base member 60 and is positioned to overlie and, hence, retain the semi-spherical ring 66. The retainer member 68 has a central opening 72 which is of greater diameter than the lower tubular member 24 and, hence, permits pivotal movement of the foot 30 about the lower end of the lower tubular member 24. This enables the foot 30 to instantly reposition itself as required to adapt to tilted or irregular surfaces so as to provide support for the amputee on such surfaces. Preferably, one or more semi-spherical insert plates 71 are provided formed of friction-resistant material, such as nylon, and are inserted between the semi-spherical ring 66 and the adjacent surface of the base member 60 and the retainer 68 to reduce friction therebetween.

The retainer member 68 has an annular flange 74 projecting upwardly about the opening 72 and the lower end 76 of a generally conical sleeve or boot 78 is secured to the annular flange 74 by suitable means, such as a hose clamp 80. The upper end 82 of the sleeve or boot 78 is secured to the lower tubular member 24 by similar means, such as hose clamp 84. The sleeve or boot 78 is formed of a resilient material, such as plastic or rubber, and permits free movement of the foot 30 to adapt to tilted or irregular surfaces, yet serves to normally urge to foot 30 to a position substantially perpendicular to the axis of the stem 20. Thus, whenever the stem 20 is raised to lift the foot 30 out of engagement with the surface, the sleeve or boot 78 immediately returns the foot 30 to its predetermined position perpendicular to the axis of the stem 20 to facilitate placement of the foot 30 in its next position. This repositioning is extremely helpful to the amputee when walking or climbing in rough terrain.

In use, the fitting and production of the socket 12 is possibly the most expensive and time consuming factor in obtaining an artificial leg. The cost of fitting a socket may run $3000 to $8000, for the socket alone, while the leg may cost an additional $1500 to $5000. The present invention enables the amputee to purchase one socket 12 having an attaching member 16 and to have a plurality of legs or stems each having attaching portions, similar to the attaching portion 18 seen in FIGS. 1 and 3, which can be quickly and easily interchanged to mate with the attaching member 16 of the socket. Thus, for example, the amputee can play golf and can enjoy the increased utility afforded by the stem 20 and semi-spherical foot 30 and, after the game, can quickly and easily exchange the stem 20 for another leg having a conventional foot to enable him to socialize in the clubhouse without the embarrassment for himself or others which the appearance of the stem 20 might create. To use the artificial leg 10 of the present invention, the amputee simply inserts his stump into the socket 12 and secures the socket by means of the straps 14. To play golf or to engage in any other activity wherein maximum functioning is required, the amputee moves the handle 40 into substantial alignment with the axis of the bolt 38 to unlock the attaching member 16, selects the stem 20 and engages the attaching projection 42 of the attaching portion 18 of the stem 20 between the fixed portion 34 and the movable portion 36 of the attaching member 16 of the socket 12. If necessary, the handle 40 can be rotated about the axis of the bolt 38 as needed to adjust the spacing between the fixed portion 34 and the movable portion 36 to the size of the attaching projection 42 of the stem 20. When the recess 52 of the attaching projection 42 of the attaching portion 18 is seated against the pin 50 of the attaching member 16, the handle 40 is returned to its position perpendicular to the axis of the bolt 38 to securely lock the stem 20 in place. Thereafter, as the amputee walks about, the foot 30 can adapt immediately to tilted or irregular surfaces and, hence, can provide maximum support for the amputee. Also, this provides a simulated "heel and toe" action which aids in walking and provides a shock-absorbing action, as well. Moreover, whenever, the amputee raises the semi-spherical foot 30 out of contact with the ground, the boot 78 will return the foot 30 to its predetermined position to assist the amputee is selecting the next position of the foot 30 so as to provide maximum support. Subsequently, when aesthetics are a consideration, the amputee can quickly and easily replace the stem 20 with an artificial leg having a conventional foot. To accomplish this, the amputee merely raises the handle 40 to the position in substantial alignment with the axis of the bolt 38. This slightly displaces the movable portion 36 away from the fixed portion 34 and, hence, immediately releases the attaching projection 42 of the stem 20. He then selects an artificial leg having a conventional foot and having an attaching plate 54 mounted above the knee joint and having an attaching projection 42 mounted on the upper surface of the attaching plate 54. The attaching projection 42 of the attaching plate 54 is positioned in the same manner as described above for the stem 20 and the handle 40 is returned to its position perpendicular to the axis of the bolt 38 which immediately clamps the projection 42 of the replacement leg in position for use.

Obviously, numerous variations and modifications can be made without departing from the spirit of the present invention. Therefore, it should be clearly understood that the form of the present invention described above and shown in the figures of the accompanying drawings is illustrative only and is not intended to limit the scope of the present invention.

What is claimed is:

1. An artificial leg comprising:
   a socket formed to receive the stump of an amputee's leg and having means for securing said socket to said amputee,
   a first member fixedly secured to said socket including a vise-like attaching member mounted on the lower end of said socket for releasably retaining a support prosthesis, and
   a second member mounted on said support prosthesis and being fixedly retainable by said attaching member to releasably clamp said support prosthesis to said socket and containing bearing means for permitting free rotation of said support prosthesis through 360° with respect to said first member.

2. The artificial leg of claim 1 wherein:
   said attaching member includes means for immediate attachment and release.

3. The artificial leg of claim 1 wherein said second member is
   formed with an attaching projection shaped for clamping engagement by said attaching member.

4. The artificial leg of claim 1 wherein:
   said support prosthesis is an artificial leg.

5. The artificial leg of claim 1 wherein:
   said support prosthesis is a stem.

6. The artificial leg of claim 1 further comprising:
   said vise-like attaching member having a fixed portion and a movable portion,
   a bolt extending through said movable portion and engaging said fixed portion,
   a handle secured to said bolt and rotatable about the axis of said bolt to move said movable portion toward and away from said fixed portion.

7. The artificial leg of claim 6 further comprising:
   said handle being rotatable in a first direction about the axis of said bolt to displace said movable portion away from said fixed portion to immediately release said support prosthesis and rotatable in a second direction about the axis of said bolt to displace said movable portion toward said fixed portion to immediately clamp said support prosthesis.

8. The artificial leg of claim 5 wherein
   said stem comprises
   a semi-spherical foot secured to the lower end of said stem.

9. The artificial leg of claim 5 wherein said stem comprises
   an upper tubular member,
   a lower tubular member telescopically mating with said upper member, and
   means for selectably varying the length of said lower member with respect to said upper member to adjust the length of said stem.

10. The artificial leg of claim 8 wherein:
    said foot comprises:
    a semi-spherical base member,
    a semi-spherical ring secured to the lower end of said stem, and
    a semi-spherical retaining member secured to said base member and positioned to overlie said ring and formed with a central opening of greater diameter than said stem.

11. The artificial leg of claim 10 further comprising:
    at least one semi-spherical plate formed of friction resistant material interposed between said ring and an adcent surface.

12. The artificial leg of claim 10 wherein:
    the peripheral chord length of said ring is substantially less than that of said base member.

13. The artificial leg of claim 10 further comprising:
    a generally conical sleeve formed of resilient material having the upper end thereof secured to said stem and having the lower end thereof secured to said retaining member to normally urge said foot to a position substantially perpendicular to said stem.

14. The artificial leg of claim 8 wherein said second member is formed with an attaching projection shaped for clamping retention by said attaching member.

15. As artificial leg as described claim 1 wherein said support prosthesis comprises
    a stem on which said (socket) second member is mounted, and
    a semi-spherical foot secured to the lower end of said stem.

16. The artificial leg of claim 15 wherein
    said attaching member includes means for immediate attachment and release.

17. The artificial leg of claim 15 wherein:
    said stem comprises:
    an upper tubular member, a lower tubular member telescopically mating with said upper member, and means for selectably varying the length of said lower member with respect to said upper member to adjust the length of said stem.

18. The artificial leg of claim 15 wherein: said foot comprises:

a semi-spherical base member, a semi-spherical ring secured to the lower end of said stem, and a semi-spherical retaining member secured to said base member and positioned to overlie said ring and formed with a central opening of greater diameter than said stem.

* * * * *